United States Patent [19]

Cohen et al.

[11] 4,107,183

[45] Aug. 15, 1978

[54] SYNTHESIS OF OPTICALLY ACTIVE CARBOXYLIC ACID ESTERS

[75] Inventors: Noal Cohen, Montclair; Gabriel Saucy, Essex Fells, both of N.J.

[73] Assignee: Hoffmann-La Roche Inc., Nutley, N.J.

[21] Appl. No.: 796,929

[22] Filed: May 16, 1977

Related U.S. Application Data

[60] Division of Ser. No. 638,722, Dec. 8, 1975, Pat. No. 4,041,058, which is a continuation-in-part of Ser. No. 544,154, Jan. 27, 1975, abandoned.

[51] Int. Cl.² .......................................... C07D 309/22
[52] U.S. Cl. ........................... 260/345.8 R; 260/410; 260/410.9 R; 260/448.2 R; 260/389; 260/395
[58] Field of Search ................. 260/410.9 R, 448.2 R, 260/410, 345.8 R, 389, 395

[56] References Cited

PUBLICATIONS

Chemical Abstracts vol. 80, No. 45789j, (1974).
Hill et al., *J. Org. Chem.* vol. 37, No. 32 (1972), pp. 3679–3709.
Sucrow et al., *Chem. Ber.* 104 (1971), pp. 3679–3709.

*Primary Examiner*—Winston A. Douglas
*Assistant Examiner*—John F. Niebling
*Attorney, Agent, or Firm*—Samuel L. Welt; Bernard S. Leon; William H. Epstein

[57] ABSTRACT

A synthesis of 2,6,10-trimethyl-undecan-1-ol, an intermediate for producing vitamin E, from methacrolein, crotonaldehyde, β-hydroxy-isobutyric acid including intermediates in this synthesis.

1 Claim, No Drawings

SYNTHESIS OF OPTICALLY ACTIVE CARBOXYLIC ACID ESTERS

CROSS REFERENCE TO RELATED APPLICATIONS

This is a division of application Ser. No. 638,722 filed 12/8/75 now U.S. Pat. No. 4,041,058, which in turn is a continuation-in-part application of U.S. application Ser. No. 544,154 filed 1/27/75, now abandoned.

This application is related to U.S. Patent application Ser. No. 417,465, filed Nov. 19, 1973, now U.S. Pat. No. 3,947,473, Scott, Parrish and Saucy, which is incorporated herein by reference.

BACKGROUND OF THE INVENTION

In the past, optically active α-tocopherol and derivatives thereof which are the 2R,4'R, 8'R isomers of compounds of the formula:

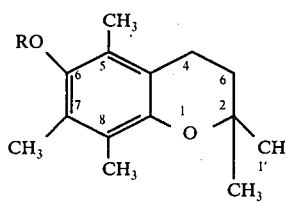

have been prepared through isolation from natural sources as vegetable oil. This procedure suffers from many drawbacks due to the fact that the tocopherol content of these oils is very small. Therefore, a great amount of oil must be processed in order to isolate a small amount of natural tocpherol. Additionally, the process whereby various tocopherols are isolated from vegetable oil is extremely cumbersome.

In U.S. Pat. No. 3,947,473 Scott et al., vitamine E active compounds have been synthesized by reacting via a Wittig reaction a compound of the formula::

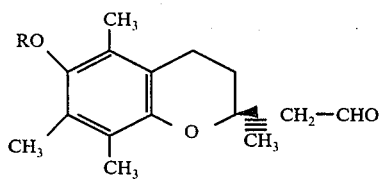

II wherein R is hydrogen or forms an ether protecting group removable by hydrogenolysis or acid catalyzed cleavage. (Please note, the compound of the formula XXVII where $n$ is 1 in U.S. Pat. No. 3,947,473 ) with a phosphonium salt prepared from a compound of the formula:

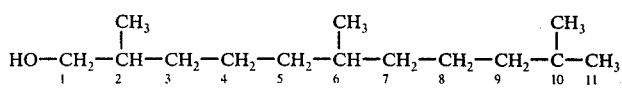

III (Please note, compound XLIV in U.S. Pat. No. 3,947,473 ). Where the compound of the formula III has a 2R, 6R configuration, i.e. a compound of the formula:

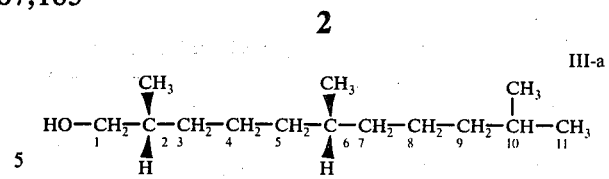

III-a then natural α-tocopherol is produced by this procedure.

In accordance with this process, it has been desired to provide a simple and economic method for preparing the compound of formula III and III-A from relatively cheap and economic starting materials.

SUMMARY OF THE INVENTION

In accordance with this invention, the compound of formula III can be prepared from either methacrolein which has the formula:

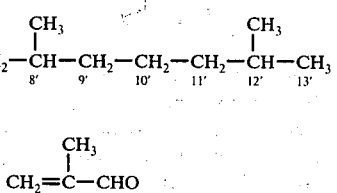

IV-A or β-hydroxy isobutyric acid which has the formula:

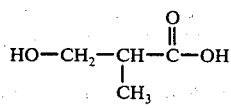

IV-B

In accordance with this invention, the compound of formula III can be produced in any desired configurations such as the following stereoconfigurations:
2R, 6R;
2RS, 6RS;
2R, 6RS; and
2RS, 6R.
depending on the optical configuration of the compound of formula IV-B.

This invention also provides a direct means for asymmetrically synthesizing the specific stereoisomer of formula III-A and consequently optically active vitamin E directly from the aforementioned starting materials without the loss of yield due to the production of an unwanted isomer.

DETAILED DESCRIPTION OF THE INVENTION

The numbering of the claims in formula I, III and III-A, above, is shown for the purpose of convenience.

As used throughout this application, the term "lower alkyl" comprehends both straight and branched chain saturated hydrocarbon groups containing from 1 to 7 carbon atoms such as methyl, ethyl, propyl, isopropyl, etc. As used throughout this application, the term "halogen" includes all four halogens, such as bromine, chlorine, fluorine and iodine. The term "alkali metal" includes sodium, potassium, lithium, etc.

When the term "cis" is utilized in this application, it designates that the two largest substituents attached across the double bond are on the same side of the double bond. The term "trans" as utilized in this application, designates that the largest substituents attached across the double bond are on opposite sides of the double bond.

In the pictorial representation of the compounds given throughout this application, a (▼) tapered line indicates a substituent which is pointed out of the plane of the paper towards the reader.

The term "lower alkoxy" as used through the specification denotes lower alkoxy groups containing from 1 to 7 carbon atoms such as methoxy, ethoxy, propoxy, isopropoxy, etc. The term "lower alkanoyl" as used throughout this specification denotes lower alkanoyl groups containing from 2 to 5 carbon atoms such as acetyl or propionyl.

As also used herein, the term "aryl" signifies mononuclear aromatic hydrocarbon groups such as phenyl, tolyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aroic acid" comprehends acids wherein the aryl group is defined above. The preferred aroic acid is benzoic acid.

As still further used herein, the term "ester protecting group removable by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl, tertiary butyl and ethyl ester, the aryl esters, particularly phenyl ester and the aryl lower alkyl esters, particuarly benzyl ester. The alcohols utilized to form the hydrolyzable ester protecting group are lower alkanols or an aryl lower alkanols or reactive derivatives thereof. Among the reactive derivatives which can be utilized to form such ester groups are the alkyl halides, preferably the chlorides or the bromides.

The term "ether protecting group removable by hydrogenolysis or acid catalyzed cleavage" designates any ether which, upon acid catalyzed cleavage or hydrogenolysis yeilds the hydroxy group. A suitable ether protecting group is, for example, the tetrahydropyranyl ether or 4-methyl-5,6-dihydro-2H-pyranyl ether. Others are arylmethyl ethers such as benzyl, benzylhydryl, or trityl ethers or alpha-lower alkoxy lower alkyl ether, for example, methoxymethyl or allylic ethers, or triaryl ethers such as trimethyl silyl ether or dimethyltert-butyl silyl ethers.

The preferred ethers which are removed by acid catalyzed cleavage are t-butyl and tetrahydropyranyl. Acid catalyzed cleavage is carried out by treatment with a strong organic or inorganic acid. Among the preferred inorganic acids are the mineral acids such as sulfuric acid, hydrohalic acid, etc. Among the preferred organic acid are lower alkanoic acids such as acetic acid, paratoluene sulfonic acid, etc. The acid catalyzed cleavage can be carried out in an aqueous medium or in an organic solvent medium. Where an organic acid is utilized, the organic acid can be the solvent medium. In the case of t-butyl, an organic acid is generally utilized with the acid forming the solvent medium. In the case of tetrahydropyranyl ethers, the cleavage is generally carried out in an aqueous medium. In carrying out this reaction, temperature and pressure are not critical and this reaction can be carried out at room temperature and atmospheric pressure.

The preferred ethers which are removable by hydrogenolysis are the aryl methyl ethers such as benzyl or substituted benzyl ethers. the hydrogenolysis can be carried out by hydrogenation in the presence of a suitable hydrogenation catalyst. Any conventional method of hydrogenation can be utilized in carrying out this procedure. Any conventinal hydrogenation catalyst such as palladium can be utilized.

In accordance with this invention, the compound of formula IV-A can be converted to the compound of the formula III via the following intermediates:

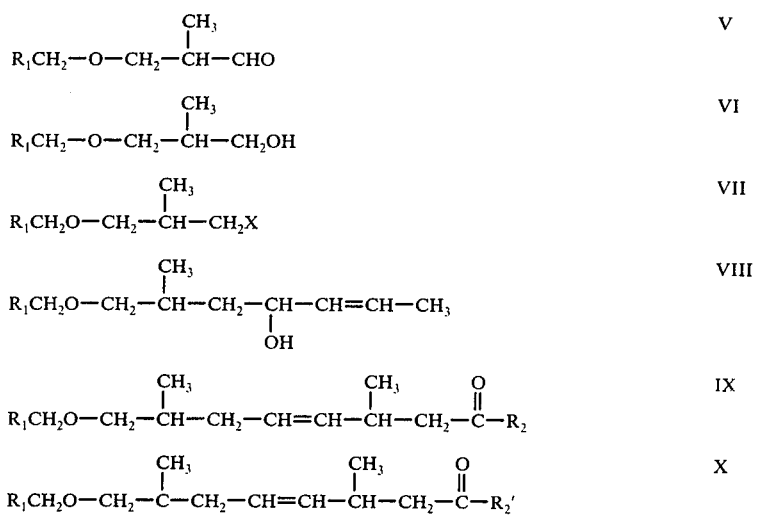

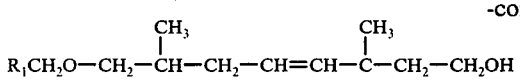 XI

 XII

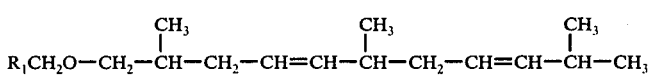 XIV wherein R₁ is aryl; R₂ is hydrogen, lower alkoxy,

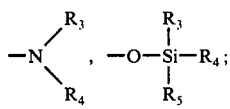

R'₂ is lower alkoxy and R₃, R₄ and R₅ are lower alkyl.

In the first step of this invention, methacrolein is reacted with an alcohol of the formula:

 XIII wherein R₁ is as above;
to produce the compound of formula V. In this reaction, the aforementioned alcohol is reacted with methacrolein in the presence of an inorganic base. Any conventional inorganic base such as an alkali metal hydroxide can be utilized to carry out this reaction. Among the preferred alkali metal hydroxides are included sodium hydroxide and potassium hydroxide. Generally this reaction is carried out in an aqueous medium. In carrying out this reaction, temperature and pressure are not critical and this reaction can be carried out at room temperature and atmospheric pressure. On the other hand, elevated or reduced temperatures can be utilized. Generally, it is preferred to carry out this reaction at temperature of between −25° C. to +20° C.

The compound of formula V is converted to the compound of formula VI by treating the compound of formula V with an alkali metal borohydride reducing agent. The temperature and pressure are not critical and this reaction can be carried out at room temperature and atmospheric pressure. In carrying out this reaction, any conventional alkali metal borohydride reducing agent such as sodium borohydride can be utilized. This reaction is carried out under the same conditions of temperature and pressure that were utilized to form the compound of formula V. Furthermore, this reaction is carried out in an aqueous medium. On the other hand, the methacrolein and the aforementioned alcohol can be directly reacted in the aqueous medium with sodium hydroxide and an alkali metal borohydride reducing agent to produce the compound of formula VI directly without isolating the compound of formula V from the reaction medium. In this case, the same temperatures and pressures previously described for the formation of the compound of formula VI from the compound of formula V can be utilized.

The compound of formula VI is converted to the compound of formula VII by treating the compound of formula VI with a halogenating agent. Any of the conditions conventional in halogenating an alcohol can be utilized to carry out this reaction. Among the conventional methods of halogenating the compound of formula VI is by treating compounds of formula VI with a halogenating agent. Among the conventional halogenating agents which can be utilized are included phosphorous tribromide, triphenyl phosphine dibromide and thionyl chloride. Any of the conditions conventional in utilizing these halogenating agents can be utilized to convert the compound of formula VI to the compound of formula VII.

In accordance with another embodiment of this invention, the compound of formula VI can be prepared in an alternate procedure from a compound of the formula

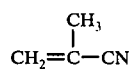 XV via the following intermediates

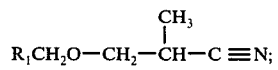 XV-A and

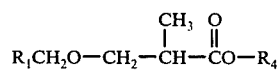 XV-B wherein R₁ and R₄ are as above.

The compound of formula XV is reacted with the compound of formula XIII to produce the compound of XV-A utilizing a conjugate addition reaction. Any of the conditions conventional in conjugate additions can be utilized in carrying out this reaction. Generally, this reaction is carried out utilizing the compound of formula XIII as the solvent medium and an alkali metal hydride. In carrying out this reaction temperature and pressure are not critical and this reaction can be carried out at room temperature and atmospheric pressure. Generally this reaction is carried out at a temperature of from 30° C. to 90° C. The compound of formula XV-A is converted to the compound of the formula XV-B by treating the compound of the formula XV-A with an inorganic acid. Generally this reaction is carried out in a lower alkanol solvent, such as methanol, ethanol, propanyl, etc. In carrying out this reaction, any conventional inert organic acid such as hydrohalic acids, sulfuric acid, etc. can be utilized. It is generally preferred to treat the compound of the formula XV-A with a lower alkanol solvent which is saturated with an inorganic acid, i.e., methanol saturated with hydrochloric acid. In carrying out this reaction, temperatures of from −30° C. to 65° C. can be utilized.

The compound of formula XV-B is converted to the compound of formula VI, via this alternative method of producing the compound of formula VI, by treatment with an aluminum hydride reducing agent. Any conventional aluminum hydride reducing agent can be utilized to carry out this reaction. Among the preferred reducing agents are the alkali metal aluminum hydrides such as lithium aluminum hydride, the alkyl aluminum hydride reducing agents such as diisobutyl aluminum hydride, diisoamyl aluminum hydride, as well as sodium dihydro-bis[2-methoxyethoxy]-aluminum hydride. The reduction with an aluminum hydride reducing agent is carried out in an inert organic solvent medium. Any conventional inert organic solvent medium can be utilized as the reaction medium. Among the preferred inert organic solvents are included pentane, tetrahydrofuran, dioxane, diethyl ether, hexane, toluene, benzene or xylene. Generally temperatures of from about −120° C. to about 30° C. are utilized in carrying out this reduction reaction.

The compound of formula VII is converted to the compound of formula VIIII via a Grignard reaction. In this reaction, the magnesium halide Grignard reagent of formula VII is prepared. This Grignard reagent is prepared utilizing the conventional procedures for forming magnesium halide Grignard reagents. This Grignard reagent of formula VII is then reacted with crotonaldehyde via a conventional Grignard reaction. In carrying out this reaction, any of the conditions conventionally utilized in Grignard reactions can be used. The Grignard reaction produces a trans double bond within the molecule of formula VIII.

In an alternative approach, the compound of formula VIII can be produced from the compound of formula VII via the following intermediates:

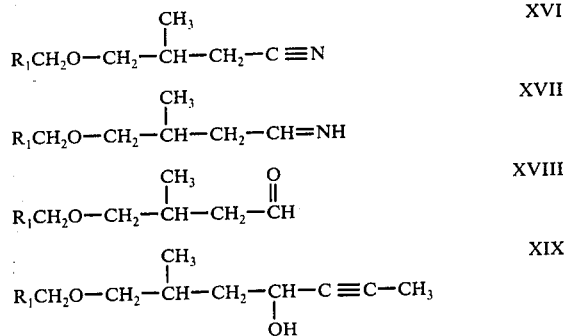

In this alternative synthesis of the compound of formula VIII, the compound of formula VII, is first treated with an alkali metal cyanide. In this manner, the compound of formula XVI is formed. This reaction is carried out by conventional procedures utilizing an aqueous lower alkanol solvent as the reaction medium. In carrying out this reaction, temperatures of from 50° C. to 100° C. are generally utilized. In the next step, the compounds of formula XVI is converted to the compound of formula XVII by treatment with diisobutyl aluminum hydride. Any of the conditions normally used to reduce nitriles to imines with diisobutyl aluminum hydride can be utilized in carrying out this reaction. The compound of formula XVII is converted to the compound of formula XVIII by acid hydrolysis. Any conventional method of acid hydrolysis can be uilized to carry out this conversion. Generally this hydrolysis reaction is carried out in an aqueous medium with an inorganic acid such as sulfuric acid, hydrochloric acid, etc. In this reaction, temperature and pressure are not critical and the hydrolysis can be carried out at room temperature or atmospheric pressure. On the other hand, elevated or reduced temperatures and pressures can be utilized in carrying out this reaction.

The compound of formula XVIII is converted to the compound of formula XIX, in the next step of this alternative synthesis, by treating the compound of formula XVIII with an alkali metal acetylide of the formula:

$$CH_3-C\equiv CM \qquad XX$$

wherein M is an alkali metal.

In carrying out this reaction, any of the procedures for reacting acetylides with aldehydes to form addition products can be utilized. In the final step of this alternative procedure, the compound of formula XIX can be converted by either one of two methods to the compound of formula VIII. These methods are either hydrogenation in the presence of a selective hydrogenation catalyst or chemical reduction with either sodium in liquid ammonia or an aluminum hydride reducing agent. The catalytic hydrogenation produces a compound of the formula VIII where the double bond formed has a cis configuration. On the other hand, chemical reduction of the compound of formula XIX produces the compound of formula VIII where the double bond formed by this chemical reduction has a trans configuration.

The compound of formula XIX is converted to the compound of the formula VIII by hydrogenation in the presence of a selective hydrogenation catalyst. Any conventional catalyst which selectively reduces only the triple bond (acetylene linkage) to a double bond can be utilized in carrying out this conversion. Among the preferred selective hydrogenation catalysts are the palladium catalysts which contain a deactivating material such as lead, lead oxide or sulfur. Among the preferred selective hydrogenation catalysts are included the palladium-lead catalyst of the type disclosed in Helvetica Chimica Acta., 35, pg. 446 (1952) and U.S. Pat. No. 2,681,938 — Lindlar. In carrying out this hydrogenation, temperature is not critical and this reaction can be carried out at room temperature. On the other hand, elevated or reduced temperatures can be utilized. Generally, this reaction is carried out in an inert organic solvent. Any conventional inert organic solvent can be utilized such as ethyl acetate, toluene, petroleum ether or hexane. The hydrogenation of a compound of the formula XIX utilizing a selective hydrogenation catalyst produces a cis configuration across the double bond formed thereby. Therefore, the subjection of a compound of the formula XIX to catalytic hydrogenation produces a compound of the formula VIII where the double bond formed by the selective hydrogenation has a cis configuration.

In accordance with this invention, the compound of formula XIX can also be converted to the compound of formula VIII by chemical reduction with either sodium in liquid ammonia or an aluminum hydride reducing agent. The chemical reduction of the compound of the formula XIX reduces the triple bond to a double bond which has a trans configuration. Hence, the compound of formula VIII is formed by this chemical reduction with the double bond having a trans configuration. Where the reduction is carried out utilizing sodium in liquid ammonia, any of the conditions conventional in this type of reduction can be utilized. Generally, this reaction is carried out at a temperature of from about −30° C. to −80° C. In this reduction, the liquid ammonia can be utilized as the reaction medium. On the other hand, a co-solvent can be present in the reaction medium along with liquid ammonia. As the co-solvent, any conventional inert organic solvent which is in liquid form at the temperature of the reaction can be utilized. Among the preferred inert organic solvents are included ether solvents such as dioxane, diethyl ether, tetrahydrofuran, etc. On the other hand, the reduction can be carried out by treating the compound of formula XIX with an aluminum hydride reducing agent. Any conventional aluminum hydride reducing agent can be utilized to carry out this reduction. Among the preferred reducing agents are the alkali metal aluminum hydrides such as sodium dihydrobis[2-methoxyethoxy]aluminum hydride. The reduction with an aluminum hydride reducing agent is carried out in an inert organic solvent medium. Any conventional inert organic solvent medium can be utilized for carrying out this reaction. Among the preferred inert organic solvents are included pentane, dioxane, diethyl ether, tetrahydrofuran, hexane, toluene, benzene or xylene. Generally, temperatures of from about $-120°$ C. to about $30°$ C. are utilized in carrying out this reduction reaction.

In accordance with this invention, when the compound of formula VIII is subjected to Claisen rearrangement, the compound of formula IX is produced via the formation of a compound of the formula:

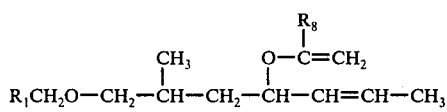

IX-A wherein $R_1$ is as above; $R_8$ is hydrogen, lower alkoxy,

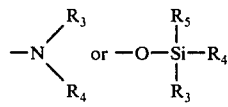

and $R_3$, $R_4$ and $R_5$ are lower alkyl;
as an intermediate.

Any of the conditions conventional in Claisen rearrangement can be utilized in carrying out the conversion of the compound of the formula VIII to form a compound of the formula IX. See Hill et al., *J. Org. Chem.*, Vol. 37, No. 32, 1972, pages 3737–3740, as well as Sucrow et al., *Che. Ber.*, 104, 3689-3709 [1971], and Sucrow and Richter, *Chem. Ber.*, 104, 3679–3688 [1971].

The compound of formula VIII is converted, via the Claisen reaction, to the compound of formula IX via the intermediate of the formula IX-A. In carrying out this reaction, any of the conditions conventionally utilized in Claisen type rearrangement reactions such as described in the above publications can be utilized. In accordance with the preferred embodiment of this invention, the Claisen rearrangement is carried out by reacting the compounds of formula VIII with any one of the following reactants:

$CH_2=CH-O-R_{10}$  XX-A

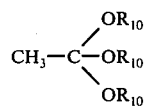  XX-B

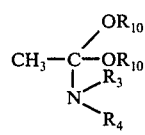  XX-C

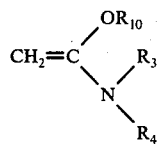 XX-D

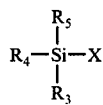 XX-E wherein $R_3$, $R_4$ and $R_5$ are as above, and $R_{10}$ is lower alkyl, and X is halogen.

The compound of formula IX where $R_2$ is hydrogen can be formed by reacting the compound of formula VIII with the vinyl ether of formula XX-A via a Claisen rearrangement reaction. Any of the conditions conventional in carrying out a Claisen rearrangement with a vinyl ether can be utilized in carrying out this reaction. Where the compound of formula XX-A is utilized, the compound of formula IX-A where $R_8$ is hydrogen is formed as an intermediate. In converting the compound of formula VIII to the compound of formula IX, the compound of formula VIII is first reacted with the vinyl ether of formula XX-A. In reacting the compound of formula VIII with the compound of formula XX-A to form the compound of formula IX-A where $R_8$ is hydrogen, temperatures of from about $40°$ C. to $150°$ C. are generally utilized. This reaction takes place in the presence of an acid catalyst. Any conventional acid catalyst can be utilized. Among the preferred acid catalysts are the inorganic acids such as phosphoric acid and the hydrohalic acids as well as acid salts such as mercuric acetate. On the other hand, conventional organic acid catalysts such as p-toluene sulfonic acid and p-nitrophenol can be utilized. This reaction can be carried out in an inert organic solvent. Any conventional inert organic solvent having a boiling point of greater than $40°$ C. can be utilized. Among the preferred solvents are the high boiling hydrocarbon solvents such as benzene, toluene, xylene, heptane, as well as ether solvents such as dimethoxyethane, diethylene glycol, dimethyl ether and dioxane. The compound of formula IX-A where $R_8$ is hydrogen is converted to the compound of formula IX where $R_2$ is hydrogen by heating to a temperature of from $80°$ C. to $200°$ C. This reaction is carried out in the absence of any catalyst. However, the same solvent medium utilized for forming the compound of the formula IX-A can be utilized in carrying out this reaction.

On the other hand, the compound of the formula VIII can be converted to the compound of formula IX where $R_2$ is lower alkoxy utilizing orthoacetates of formula XX-B. In carrying out this reaction, any of the conditions conventionally utilized in Claisen rearrangements with an orthoacetate can be utilized. In this reaction, the compound of formula IX-A where $R_8$ is lower alkoxy forms as an intermediate. Under the condition of the reaction, the compound of formula IX-A where $R_8$ is lower alkoxy rearranges to produce the compound of formula IX where $R_2$ is lower alkoxy. In carrying out this reaction, temperatures of from $140°$ C. to $250°$ C. are generally utilized. This reaction is carried out in the presence of excess of the orthoacetate of formula XX-B. This is true since the orthoacetate can be utilized as the solvent medium. On the other hand, the reaction can take place in an inert organic solvent. Generally those solvents having a boiling point of greater than 140° C. are preferred. Generally, it is preferred to carry out this reaction in the presence of a lower alkanoic acid. If desired, the lower alkanoic acid is present in molar amounts of from 1% to 10% per mole of the compound of the formula VIII.

Where it is desired to produce the compound of formula IX where $R_2$ is

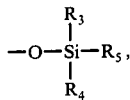

the compound of formula VIII is first converted to a compound of the formula:

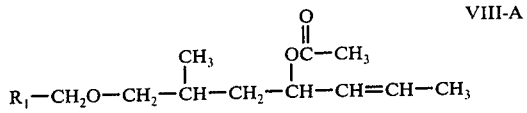

VIII-A by acylation with acetic acid or a reactive derivative thereof. Any conventional method of acylating a hydroxy group with an acetyl group can be utilized to carry out this conversion. Among the preferred methods is to react the compound of formula VIII with a reactive derivative of an acetic acid such as a halide derivative or an anhydride derivative. In the next step, the compound of formula VIII-A is converted to its enolate form, i.e., a compound of the formula:

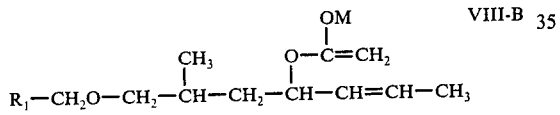

VIII-B wherein M is as above;
by treatment with an alkali metal alkyl amide base. Any conventional alkali metal alkyl amide base can be utilized. The alkyl moiety can be a lower alkyl or cycloalkyl moiety which contains from 5 to 7 carbon atoms. Among the preferred bases are lithium cyclohexylisopropyl amide and lithium diisopropylamide.

The enolate of formula VIII-B are then reacted with the silyl halide of the formula XX-E to form the compound of the formula IX via a Claisen reaction. In this reaction, the compound of the formula IX-A is formed, where $R_8$

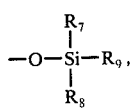

as an intermediate. This reaction to produce the compound of formula IX-A takes place in an inert organic solvent medium at temperatures of from −10° C. to −110° C. In carrying out this reaction, any conventional inert organic solvent which will not freeze at the reaction temperature can be utilized. Among the preferred solvents are tetrahydrofuran, diethyl ether, dioxane and dimethoxyethane.

The compound of the formula IX-A where $R_8$ is

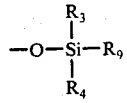

is converted to the corresponding compound of the formula IX by warming this compound in the reaction medium in which it was formed to a temperature of from 0° C. to 40° C. Therefore, in accordance with this invention, there is no need to isolate the compound of formula IX-A from the reaction mixture. The reaction mixture containing the compound of formula IX-A can be warmed to a temperature of from 0° C. to 40° C. for form the compound of the formula IX. The compound of formula IX-A can, if desired, be isolated from the reaction mixture before warming.

Where it is desired to produce the compound of formula IX where $R_2$ is

the compound of formula VIII is reacted with a compound of formula XX-C or formula XX-D or mixtures thereof utilizing conditions conventional in Claisen reactions with amides. In this reaction, the compounds of the formula IX-A where $R_8$ is

forms as an intermediate. This intermediate is instantaneously converted to the compound of formula IX under the conditions of the reaction. This reaction is carried out at temperatures of from 120° C. to 250° C. in an inert organic solvent. Any conventional inert organic solvent can be utilized to carry out this reaction with high boiling solvents, i.e., solvents being above 150° C. being preferably utilized. Among the conventional inert organic solvents are included xylene and diglyme.

Where $R_2$ in the compound of formula IX is other than hydrogen or lower alkoxy, the compound of formula IX can be converted to the compound of formula X by first hydrolyzing the silyl ester or amide group and then esterifying the free hydroxy group with a lower alkanol or reactive derivatives thereof. Any conventional method of silyl ester or amide hydrolysis and esterification can be utilized to affect this conversion. On the other hand, the compound of formula IX where $R_2$ is lower alkoxy is the compound of formula X. Where $R_2$ is hydrogen, in the compound of formula IX, this compound is the compound of formula XII.

The compound of formula X is converted to the compound of the formula XI by reduction with an aluminum hydride reducing agent. This reaction is carried out in the same manner as described in connection with the conversion of a compound of the formula XV-B to the compound of the formula VI. The compound of the formula XI is converted to the compound of the formula XII by treating the compound of the formula XI with an oxidizing agent, capable of converting an alcohol to an aldehyde. Any of the conventional oxidizing agents for converting alcohols to aldehydes can be utilized in this process. The preferred oxidizing agents for use in this type of conversion is a chromium trioxide-pyridine complex. Generally, this preferred oxidation is carried out in a halogenated hydrocarbon solvents such as chloroform, methylene chloride, etc. In carrying out this reaction, temperature and pressure are not critical and this reaction can be carried out at room temperature and atmospheric pressure. On the other hand, elevated temperatures as well as reduced temperatures can be utilized in carrying out this oxidation.

The compound of formula XII is converted to the compound of formula XIV by reacting the compound of formula XII with a phosphorane of the formula:

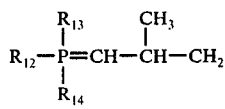    XXI wherein $R_{12}$, $R_{13}$ and $R_{14}$ are aryl.

This reaction is carried out by a conventional Wittig type reaction. Any of the conditions conventional in Wittig type reactions can be utilized to convert the compound of formula XII to the compound of formula XIV.

The compound of formula XIV is converted to the compound of formula III by hydrogenation. Any conventional method of hydrogenation can be utilized to carry out this reaction. Generally, it is preferred to carry out this reaction by hydrogenating the compound of formula XIV in the presence of a noble metal catalyst such as palladium. While palladium is preferred, any conventional noble metal catalyst can be utilized to carry out this reaction. Any of the common supports for noble metal catalysts can be utilized in accordance with this invention. Among the preferred catalyst supports for use in this invention are supports such as carbon, charcoal, barium sulfate, etc. In carrying out this hydrogenation reaction, any of the conventional inert organic solvents can be utilized. In carrying out this reaction, temperature and pressure are not critical and this reaction can be carried out at room temperature and atmospheric pressure. On the other hand, higher or lower temperatures can be utilized. This hydrogenation besides reducing the double bond also cleaves the ether linkage to form the compound of formula III.

In accordance with another embodiment of this invention, the compound of formula VI where the $R_1CH_2$ substituent is replaced by $R_{11}$, where $R_{11}$ taken together with its attached oxygen atom forms an ether protecting group convertable to hydroxy by acid catalyzed cleavage, can be produced from beta-hydroxy isobutyric acid via a compound of the formula

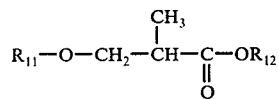    XXV wherein $-OR_{11}$ forms an ether protecting group convertable to hydroxy by acid catalyzed cleavage; and $-OR_{12}$ forms an ester protecting group convertable to hydroxy by hydrolysis.

In forming the compound of formula XXV, beta-hydroxy isobutyric acid is esterified and etherified so that both its free hydroxy groups are protected. In this step, the free $-CH_2OH$ group is etherified to form a cleavable ether while the free

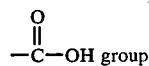

is esterified to form a hydrolyzable ester. The cleavable ether and the hydrolyzable ester group can be formed separately. On the other hand, the ether and ester may be formed in one step by reacting the hydroxy acid with isobutylene in the presence of an inorganic acid and boron trifluoride etherate. This reaction can be carried out at temperatures such as $-100°$ C. to $30°$ C. By this reaction, the acid is esterified with a tertiary butyl group and the hydroxy group is etherified with a tertiary butyl group.

Among the preferred cleavable ether groups are included tetrahydropyranyl. In forming this ether, any of the conventional conditions utilized in reacting hydroxy groups with activated alcohol derivatives can be utilized. On the other hand, the acid group of beta-hydroxy isobutyric acid can be esterified by reacting the acid with an alcohol. Any of the conditions conventional in forming esters can be utilized to carry out this reaction. Among the preferred esters are those where the $R_{12}$ is a lower alkyl group.

The compound of the formula XXV is converted to the compound of formula VI (where $R_1CH_2O-$ is replaced by $-OR_{11}$ and $R_{11}$ is defined as above) by treating the compound of formula XXV with an aluminum hydride reducing agent. Any of the conventional aluminum hydride reducing agents such as disclosed in connection with the conversion of a compound of the formula XV-B to a compound of the formula VI can be utilized in this reaction. Furthermore, any of the conditions described in connection with the conversion of a compound of the formula XV-B to a compound of the formula VI can also be utilized in this reaction.

Where it is desired to produce the compound of formula III with a 2R or 2S configuration, the beta-hydroxy isobutyric acid having the proper configuration about the asymmetric carbon atom is utilized. For instance, where the compound of formula III having a 2R configuration is desired, the compound of the formula

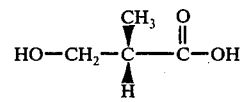    IV-B$_1$ i.e., S-(+)-beta-hydroxy isobutyric acid is utilized as a starting material. The configuration about this asymmetric atom in the compound of the formula IV-B$_1$ is maintained throughout the various intermediates in the conversion to the compound of formula III.

During the conversion of a compound of formula VI to a compound of formula III, the $R_1CH_2O-$ group in the various intermediates formed during this conversion is replaced by $-OR_{11}$ with $R_{11}$ being defined as above.

Where $R_1CH_2O-$ is replaced by $R_{11}O-$ in the compound of formula XVII, this compound has the formula

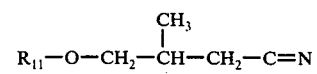    XVII-A where $R_{11}$ is as above.

The compound of formula XVII-A is converted to the corresponding compound of formula XVIII, i.e., a compound of the formula

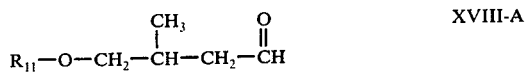
XVIII-A by acid hydrolysis so as not to cleave the protecting group formed by $R_{11}O$. This hydrolysis is carried out in an aqueous medium at a pH of from 4 to 5. Any weak acid which provides a pH of from 4 to 5 can be utilized in this reaction. The preferred weak acid is ammonium chloride. In this reaction, temperature and pressure are not critical and the hydrolysis can be carried out at room temperature and atmospheric pressure. If desired, higher and lower temperatures can be utilized.

Where $R_1CHO-$ is replaced by $R_{11}O-$ in the compound of formula XIV, hydrogenation of this compound produces a compound of the formula

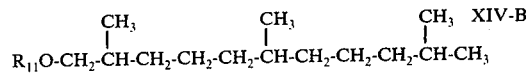
XIV-B wherein $R_{11}$ is as above.

The compound of formula XIV-B is converted to the compound of formula III by acid catalyzed cleavage as described above.

In the compound of formula X wherein $R_1CH_2O-$ is replaced by $R_{11}O-$, i.e., the compound of the formula X-A, this compound can be converted in accordance with one embodiment of this invention, to the compound of formula III via the following intermediates:

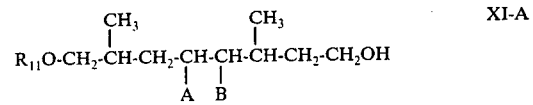
XI-A

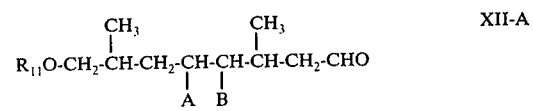
XII-A

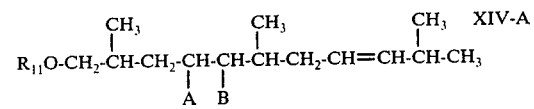
XIV-A wherein $R_{11}$ is as above and A and B are individually hydrogen or taken together form a carbon to carbon bond.

The compound of formula X-A is converted to the compound of formula III in the same manner as described in connection with the conversion of a compound of the formula X to a compound of the formula III. However, in these reactions the double bond in the compound of formula X-A, can, if desired, be reduced by hydrogenation. On the other hand, the double bond formed by A and B can be reduced at anytime during the conversion of the compound of formula XI-A to the compound of formula III. This reduction can be carried out by hydrogenation in the manner described in connection with the conversion of a compound of the formula XIV to a compound of the formula III.

Where it is desired to produce the isomer of formula III-A, the compound of formula IV-B$_1$ is utilized as a starting material to produce the compound of formula XIX which has the following configuration:

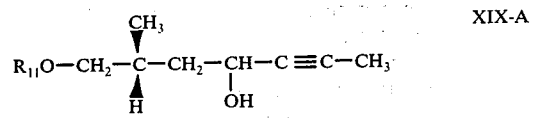
XIX-A wherein $R_{11}$ is as above.

The compound of the formula XIX-A can be separated into its two epimers:

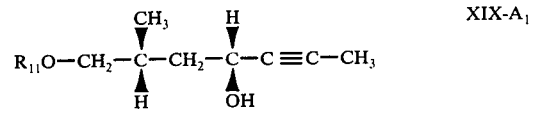
XIX-A$_1$

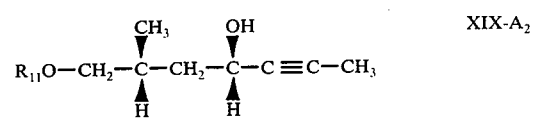
XIX-A$_2$ wherein $R_{11}$ is as above by chromatography such as high pressure liquid chromatography. Any conventional method of high pressure liquid chromatography can be utilized to make this separation. In accordance with this invention, the epimers of the formula XIX-A$_1$ and XIX-A$_2$ can be converted to the compound of formula IX of the following configuration:

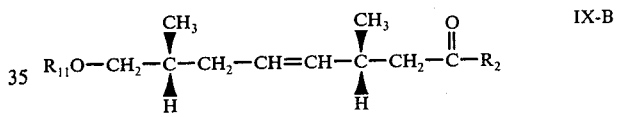
IX-B wherein $R_{11}$ and $R_2$ are as above;
via the following intermediates:

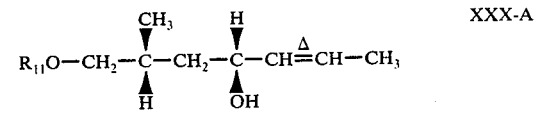
XXX-A

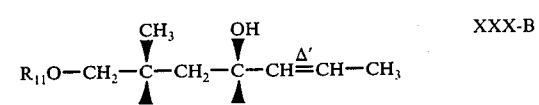
XXX-B

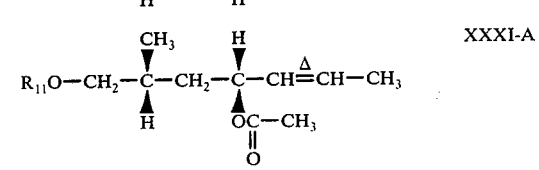
XXXI-A

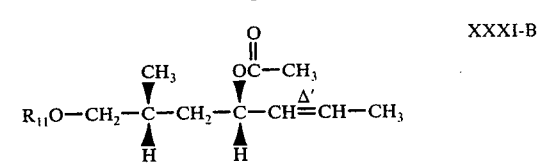
XXXI-B

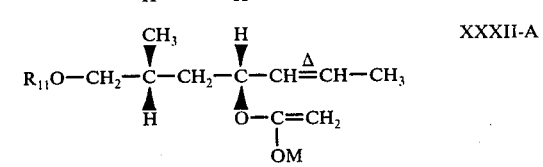
XXXII-A

-continued

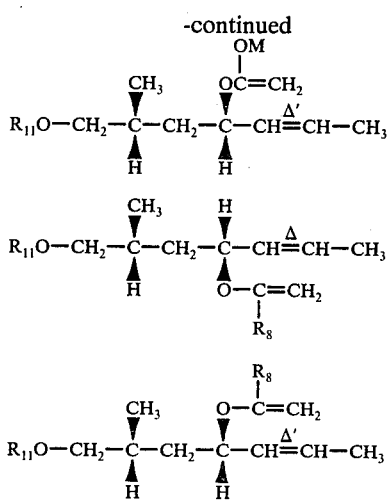

wherein $R_8$, $R_{11}$ and M are as above;
$\Delta$ denotes a trans configuration and
$\Delta'$ denotes a cis configuration.

The compound of formula XIX-A$_1$ is converted to the compound of the formula XXX-A by chemical reduction with either sodium in liquid ammonia or an aluminum hydride reducing agent as described in connection with the conversion of a compound of the formula XIX to the compound of the formula VIII. The chemical reduction produces the compound of formula XXX-A where the double bond formed by this selective hydrogenation has a trans configuration. On the other hand, the compound of the formula XIX-A$_2$ is converted to the compound of the formula XXX-B by catalytic hydrogenation with a selective hydrogenation catalyst as described in connection with the conversion of the compound of the formula XIX to a compound of the formula VIII. This catalytic hydrogenation produces a double bond with a cis configuration.

Where either the compound of the formula XXX-A or XXX-B is subjected to a Claisen rearrangement via the intermediates of the formula XXXI-A, XXXI-B, XXXII-A, XXXII-B, XXXIII-A and XXXIII-B, the specific optical isomer of the compound of formula IX-B is produced. In accordance with the claimed invention, the subjection of either of the compound of the formula XXX-A or XXX-B to Claisen rearrangement produces a single optical isomer. In order to achieve this result, it is necessary that the compound of formula XXX-A be separated from the compound of formula XXX-B. Without this separation, the specific isomer of formula IX-B will not be produced upon Claisen rearrangement. In accordance with this process, the compound of formula IX-B is produced without discarding any unwanted isomer.

The compounds of XXX-A and XXX-B are both converted to the compound of formula IX-B via a Claisen rearrangement with any one of the reactants of formula XX-A, XX-B, XX-C, XX-D or XX-E. This reaction is carried out in the same manner as described in connection with the conversion of a compound of the formula VIII to the compound of the formula IX. Where a compound of the formula XXX-A is utilized, the compound of the formula XXXIII-A forms as an intermediate. On the other hand, where the compound of formula XXX-B is utilized in this claisen rearrangement, the compound of formula XXXIII-B forms as an intermediate.

In accordance with this invention, it has been discovered that Claisen rearrangement is carried out without any cleavage of the ether group $R_{11}O-$ even though this ether group is removable by acid catalyzed cleavage. This is completely unexpected since many of the Claisen type reactions are carried out with acids and under conditions which would normally cleave the ether group $-OR_{11}$. This is extremely advantageous since the Claisen reaction leaves the hydroxy group protected for future reactions without the need for a separate reaction step for reprotecting the hydroxy group so that further reactions can be carried out. Where a compound of formula XX-E is utilized as the rearrangement agent in the Claisen reaction, the compound of formula XXX-A and XXX-B is first reacted with an acetylating agent to form the compound of formula XXXI-A and XXXI-B. This acetylation is carried out in the same manner as described hereinbefore in connection with the conversion of a compound of the formula VIII to a compound of the formula VIII-A. In the next step prior to reaction with the rearranging agent of the formula XX-E, the compound of the formula XXXI-A or XXXI-B is converted into its enolate forms, i.e., the compound of formula XXXII-A and XXXII-B respectively. These enolate forms are produced in the same manner as described in connection with the conversion of the formula VIII-B. It is these enolates which are then reacted with the compound of the formula XX-E to form the compound of the formula IX-B. This reaction is carried out in the same manner as described in connection with the reaction of a compound of the formula XX-E with a compound of the formula VIII-B to form the compound of the formula IX.

The compound of the formula IX-B is converted to the compound of the formula III-A in the same manner as described in connection with the conversion of a compound of the formula IX to a compound of the formula III. In the intermediates which form, i.e., the compounds of the formula X, XI, XII and XIV, the same configuration is maintained about both of the asymmetric carbon atoms throughout the conversion and formation of these intermediates.

In accordance with another embodiment of this invention, the compound of formula XI or XI-A can be converted to the compound of formula XIV or XIV-A via the condensation of a compound of the formula:

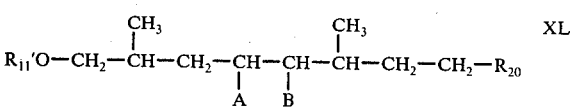

with a compound of the formula:

wherein A and B are as above; one of $R_{20}$ and $R_{21}$ is $-MgX$ and the other is $OR_{22}$; X is halogen and $-OR_{22}$ is a leaving group; and $R'_{11}$ forms with its attached oxygen moiety an ether protecting group removable by hydrogenolysis or acid catalyzed cleavage; with the proviso that when $R'_{11}$ forms an ether protecting group removable by hydrogenolysis; A and B form a carbon to carbon bond.

The compound of formula XI or XI-A can be converted to the compound of formula XL where —OR$_{20}$ is a leaving group by utilizing any conventional method of converting a hydroxy group to a leaving group. Among the preferred methods is to react the compound of formula XIV or XIV-A with an aryl sulfonyl halide as a naphthylsulfonyl halide, p-toluene sulfonyl halide, etc. or a lower alkyl sulfonyl halide, methylsulfonyl halide in the presence of an organic amine base such as pyridine, trimethyl amine, etc. In accordance with this invention, when R$_{21}$O in the compound of formula XLI is —OR$_{22}$, this compound can be prepared from:

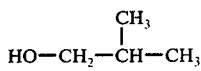
XLI-A in the same manner as described in connection with the conversion of a compound of the formula XI-A to a compound of the formula XL.

The compound of formula XL, where R$_{20}$—MgX can be prepared from the compound of formula XI or XI-A utilizing any conventional method of preparing a Grignard reagent. In the same manner, the compound of formula XLI where R$_{21}$ is MgX is prepared from the compound of formula XLI-A.

In the compounds of formulae XL or XLI, —OR$_{22}$ can be any conventional leaving group. Among the preferred leaving groups formed by —OR$_{22}$ are alkyl sulfonyloxy such as methylsulfonyloxy, aryl sulfonyloxy, such as p-toluenesulfonyloxy, naphthyl-sulfonyloxy, etc.

The compound of formula XL and XLI are reacted to form the compound of formula XIV-A in the presence of a di(alkali metal) tetrahalocuprate utilizing the procedure disclosed by Fouquet and Schlosser on pages 82 and 83 of *Angew Chem Internat. Edit.* Vol. 13 (1974). In the procedure disclosed by Fouquet and Schlosser, carbon to carbon linkage of hydrocarbons is carried out through the reaction of a magnesium halide with a sulfonyl ester. In accordance with this invention, it has been discovered that this reaction can be carried out with an ether functional group so that either the magnesium halide or sulfonyl ester can carry these functional groups. In accordance with this invention, it has been discovered that the ether group does not interfere with the reaction. In this reaction, any conventional di(alkali metal)tetrahalocuprate can be utilized with dilithium tetrachlorocuprate being preferred. Generally, this reaction is carried out in the presence of an ether solvent. Any conventional inert organic ether solvent can be utilized. Among the preferred solvents are included tetrahydrofuran, dioxane, diethyl ether, dimethoxyethane, diglyme, etc.

Intermediates of the formula VI, VII and XXV due to their fragrance are also useful as odorants or as additives to odorant compositions. Among these intermediates, the following are particularly noted:

A compound of the formula:

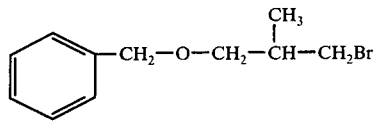

which has an almond, cinnamon, benzaldehyde and cherry odor;

A compound of the formula:

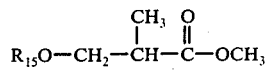

wherein R$_{15}$ is tertiary butyl;
which has a lavendin, fruity, woody odor;
A compound of the formula:

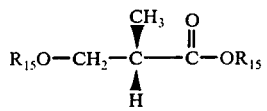

wherein R$_{15}$ is as above;
which has a fruity, rosey odor.
A compound of the formula

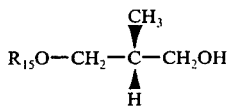

wherein R$_{15}$ is as above;
which has a hay minty, animal, coumarin odor.
A compound of the formula:

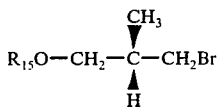

wherein R$_{15}$ is as above;
which has a fruity, medicinal, woody odor.

The intermediates of formulae VI, VII and XXV are distinguished by their particular odor properties. On the basis they can be used for perfumery purposes such as manufacture of perfumes or for perfuming products of all kinds such as cosmetic articles (soaps, powders, creams, lotions, etc.). The content of compounds of formula LIII through LVI in odorant compositions is governed by the intended use and can vary within wide limits, for example between 0.005–30-wt. percent.

As stated hereinabove, the novel odorant compositions produced in accordance with the present invention which have excellent odor properties, may be utilized in a wide range of odor compositions containing them. Preferable, however, they are utilized in amounts ranging from about 0.5 to about 20% by weight in the compositions comprising them. And, for example, when utilized for the perfuming of soaps, between 1 and 2% by weight of such perfume compositions will suffice. In compositions such as lotions, suitably hand lotions and the like, from between 2 to about 3% by weight of such compositions are utilized and in bath salts and essences, depending on the type of composition, between 0.3 and 5% by weight of the composition are utilized.

The following examples are illustrative but not limitative of the invention. All temperatures are in degrees Centigrade and the ether is diethyl ether. The 5% palladium designates a catalyst containing 5% by weight palladium on 95% by weight carbon. The term "Lindlar catalyst" designates a catalyst prepared from palladium chloride, calcium carbonate and lead acetate as described in Organic Synthesis Collective Volume 5, page 880–893 (1973). The term "Celite" designates diatomaceous earth.

EXAMPLE 1

Rac. 3-benzyloxy-2-methyl-1-propanol

A solution of 1.59 g. of sodium hydroxide and 1.6 ml. of water in 402 ml. (420 g; 3.89 moles) of benzyl alcohol was stirred and cooled to −10° C. while 100 ml. (83.7 g.; 1.19 moles) of freshly distilled methacrolein were added dropwise keeping the temperature between −10° C. and −5° C. After the reaction mixture had stirred for 0.5 hr. at −10° C., a solution of 44.9 g. (1.19 moles) of sodium borohydride in 180 ml. of water was added dropwise over 1.75 hr. keeping the temperature below 5° C. Stirring was continued for an additional hour during which time the reaction mixture was allowed to warm to room temperature. The resulting mixture was poured into ice-water and the organic materials were extracted several times with ether. The ether extracts were worked up by first combining the extracts washing with saturated brine and drying over anhydrous magnesium sulfate. After filtration and removal of the solvents in vacuo, the residue was carefully fractionated, giving, after removal of low boiling materials, 39.6 g. of rac. 3-benzyloxy-2-methyl-1-propanol as a colorless liquid, b.p. 91°–98° C. (0.5 mm Hg.).

EXAMPLE 2

Rac. 3-benzyloxy-2-methyl-1-propyl bromide

A solution of 39 g. (0.216 mole) of rac. 3-benzyloxy-2-methyl-1-propanol and 56.7 g. (0.216 mole) of triphenylphosphine in 216 ml. of dry dimethylformamide was stirred while 11.7 ml. (34.4 g.; 0.216 mole) of bromine was added dropwise, over a 15 min. period, keeping the temperature below 55° C. A few additional drops of bromine were added, until a yellow color persisted. After cooling to 30° C., the reaction mixture was poured into water and hexane was added. The precipitated triphenylphosphine oxide was filtered and washed with hexane. The filtrate and washes were combined and separated into aqueous and organic phases. The aqueous phase was extracted once with hexane, then the hexane solutions were combined, washed with 10% by weight aqueous NaHSO₃ and brine and dried. The organic solution was filtered and concentrated in vacuo giving 44.2 g. of residue which was distilled under high vacuum. There was obtained 42.3 g. of crude bromide as a colorless liquid, b.p. 73°–86° C. (0.05–0.1 mm Hg.). This material was dissolved in benzene and absorbed on 500 g. of silica gel. Elution with 5.2 l. of benzene gave after solvent removal, 38 g. of residue. This material was distilled using a Vigreaux column yielding 37.1. g. (70.7%) of pure rac. 3-benzyloxy-2-methyl-1-propyl bromide as a colorless liquid, b.p. 78°–85° C. (0.05 – 0.1 mm Hg.).

EXAMPLE 3 rac. E-1-benzyloxy-2-methyl-5-hepten-4-ol

A slurry of 0.55 g. (0.0236 mole) of magnesium powder in 15 ml. of anhydrous tetrahydrofuran was stirred and heated at reflux while a few drops of a solution of 5 g. (0.0206 mole) of rac. 3-benzyloxy-2-methyl-1-propyl bromide in 30 ml. of anhydrous tetrahydrofuran was added followed by a crystal of iodine. After the Grignard reaction had begun, the remainder of the bromide solution was added dropwise over 35 min. at reflux temperature. The reaction mixture was stirred and heated under reflux for an additional hour then cooled to 0°–5° C. (ice bath) while a solution of 1.56 g. (0.022 mole) of crotonaldehyde in 15 ml. of anhydrous tetrahydrofuran was added over a 15 min. period. After stirring at room temperature for 2.5 hours, the reaction mixture was poured onto saturated aqueous ammonium chloride and the product was extracted with ether and worked up as in Example 1. The residue (4.62 g.) was chromatographed on 250 g. of silica gel. Elution with 4:1 parts by volume and 2:1 parts by volume hexane-ether gave 3.36 g. of rac. E-1-benzyloxy-2-methyl-5-hepten-4-ol as a pale yellow oil, b.p. 110°–120° C. (bath temperature) (0.075 mm Hg.).

EXAMPLE 4 rac. Ethyl-8-benzylozy-3,7-dimethyl-4-octenoate

A solution of 1.1g (4.7 mmoles) of rac. E-1-benzyloxy-2-methyl-5-hepten-4-ol and 34.8 mg. (0.47 mmole) of propionic acid in 5.3 g. (32.9 mmoles) of triethyl orthoacetate was stirred and heated in an oil bath until distillation began. Distillation was continued until the internal temperature reached 150° C. then the solution was maintained at reflux for 3.25 hours. After cooling, the reaction mixture was treated with water and the product was isolated with ether and worked up as described in Example 1 (the ether extracts were additionally washed with aqueous sodium bicarbonate solution). The crude product was evaporatively distilled giving 1.29 g. (87.5%) of rac. ethyl 8-benzyloxy-3,7-dimethyl-4-octenoate as a pale yellow oil, b.p. 123°–132° C. (bath temperature) (0.075 mm Hg.).

EXAMPLE 5 rac. 4-Benzyloxy-3-methylbutyronitrile

A solution of 3.38 g. (0.069 mole) of sodium cyanide and 8.4 g. (0.0345 mole) of rac. 3-benzyloxy-2-methyl-1-propyl bromide in 11.5 ml. of water and 45 ml. of ethanol was stirred and heated at reflux for 20 hours. The reaction mixture was cooled, diluted with water and the product was isolated by extraction with benzene and worked up as in Example 1. This afforded 6.4 g. of oily residue which was chromatographed on 350 g. of silica gel. Elution with 4:1 parts by volume and 2:1 parts by volume hexane-ether gave 5.8 g. (89%) of pure rac. 4-benzyloxy-3-methylbutyronitrile as a yellow oil.

EXAMPLE 6 rac. 4-Benzyloxy-3-methylbutanal

A solution of 5.8 g. (0.0307 mole) of rac. 4-benzyloxy-3-methylbutyronitrile in 290 ml. of hexane was stirred at −65° C. to −70° C. while 22.4 ml. (4.78 g.; 0.0337 mole) of 25% diisobutylaluminum hydride solution in toluene was added dropwise. The resulting solution was stirred at −65° C. to −70° C. for 0.5 hours then at room temperature for 5 hours whereupon 2.8 ml. of ethyl formate was added dropwise. The reaction mixture was then treated with 250 ml. of saturated aqueous ammonium chloride solution. Stirring was continued for 20 minutes at which point 125 ml. of 5% by weight aqueous sulfuric acid was added and stirring was continued for an additional 10 minutes. The organic layer was separated and the aqueous layer was extracted with ether. The organic solutions were combined and processed as in Example 1 giving 4.79 g. (81.3%) of rac. 4-benzyloxy-3-methylbutanal as a yellow oil.

EXAMPLE 7 rac. 1-Benzyloxy-2-methylhept-5-yn-4-ol

A mixture of 72.8 ml. (0.146 mole) of 2 M n-butyllithium solution in hexane and 420 ml. of anhydrous tetrahydrofuran was stirred and cooled to −50° C. while 112 ml. of liquified methylacetylene was added dropwise from a dry ice cooled addition funnel. After the solution was complete, the reaction mixture was allowed to warm to reflux temperature (8° C.) (dry ice condenser) and stirred at this temperature for 1 hour. The white slurry was then cooled to 0° C. and stirred while a solution of 14 g. (0.0728 mole) of rac. 4— benzyloxy-3-methylbutanal in 125 ml. of anhydrous tetrahydrofuran was added dropwise. After stirring at 0° C. for 1 hour, the mixture was slowly warmed to 40° C. and stirred at this temperature for 1 hour whereupon the reaction mixture was treated with saturated aqueous ammonium chloride. The product was isolated by ether extraction and worked up as in Example 1. There was obtained 15.4 g. of crude material which was chromatographed on 400 g. of silica gel. Elution with 2:1 parts by volume and 1:1 parts by volume hexane:ether afforded rac. 1-benzyloxy-2-methylhept-5-yn-4-ol as a yellow oil.

EXAMPLE 8 rac. Z-1-Benzyloxy-2-methyl-5-hepten-4-ol

A mixture of 1 g. (4.31 mmoles) of rac. 1-benzyloxy-2-methylhept-5-yn-4-ol, 0.1 g. of Lindlar catalyst, 0.04 ml. of quinoline and 30 ml. of hexane was stirred in an atmosphere of hydrogen, at room temperature, for 40 minutes during which time approximately one equivalent of hydrogen was taken up. The catalyst was filtered and washed with hexane then the combined filtrate and washes were concentrated in vacuo giving 1.05 g. of oily product. This material was chromatographed on 50 g. of silica gel. Elution with 2:1 parts by volume and 1:1 parts by volume hexane-ether afforded 0.844 g. of a pale yellow oil. Evaporative distillation gave rac. Z-1-benzyloxy-2-methyl-5-hepten-4-ol as a colorless oil, b.p. 113°–123° C. (bath temperature) (0.25 mm Hg.).

EXAMPLE 9 rac. E-8-Benzyloxy-3,7-dimethyl-4-octen-1-ol

A suspension of 0.432 g. (11.36 mmoles) of lithium aluminum hydride in 20 ml. of anhydrous ether was stirred with ice bath cooling while a solution of 1.73 g. (5.68 mmoles) of rac. ethyl 8-benzyloxy-3,7-dimethyl-4-octenoate in 20 ml. of anhydrous ether was added over a 25 minute period keeping the temperature at 0°–5° C. The cooling bath was removed and the reaction mixture was stirred at room temperature for 2.5 hours at the end of which time 1.6 ml. of saturated sodium sulfate solution was cautiously added with ice bath cooling. After stirring for 16 hours at room temperature, the slurry was filtered on Celite and the filter cake was washed thoroughly with ether. Concentration in vacuo of the combined filtrate and washes yielded 1.46 g. of a colorless oil. This material was chromatographed on 50 g. of silica gel. Elution with 2:1 parts by volume, 1:1 parts by volume and 1:2 parts by volume hexane-ether afforded 1.38 g. of rac. E-8-benzyloxy-3,7-dimethyl-4-octen-1-ol which was evaporatively distilled giving 1.37 g. (92%) of colorless oil, b.p. 107°–108° C. (bath temperature) (0.03 mm Hg.).

EXAMPLE 10 rac. E-8-Benzyloxy-3,7-dimethyl-4-octenal

To a solution of 1.19 g. of pyridine in 15 ml. of dichloromethane was added 0.6 g. (6 mmoles) of chromium trioxide. The borwn mixture was stirred at room temperature for 15 minutes, then treated with a solution of rac. E-8-benzyloxy-3,7-dimethyl-4-octen-1-ol (0.262 g; 1 mmole) in 3 ml. of dichloromethane. After stirring at room temperature for 15 minutes, the dichloromethane solution was decanted from the dark tarry residue then the residue was washed three times with fresh dichloromethane. The dichloromethane solutions were combined and washed with 1 N aqueous sodium hydroxide, 1 N aqueous hydrochloric acid, saturated aqueous sodium bicarbonate solution and brine then dried, filtered and concentrated in vacuo. The residue (0.255 g.) was chromatographed on 10 g. of silica gel. Elution with 9:1 parts by volume and 4:1 parts by volume hexane-ether gave 0.196 g. (75.5%) of pure rac. E-8-benzyloxy-3,7-dimethyl-4-octenal. Evaporative distillation yielded a colorless liquid, b.p. 90°–93° C. (bath temperatire) (0.1 mm Hg.).

EXAMPLE 11 rac. Benzyl 2,6,10-trimethylundeca-4,8-dien-1-yl ether

A suspension of 1.52 g. (3.42 mmoles) of isobutyltriphenylphosphonium iodide in 30 ml. of anhydrous tetrahydrofuran was stirred and cooled to 0° C. while 1.55 ml. (3.42 mmoles) of n-butyllithium solution in hexane was added. The resulting red solution was stirred for 10 minutes at room temperature then treated with a solution of rac. E-8-benzyloxy-3,7-dimethyl-4-octenal (0.594 g.; 2.28 mmoles) in 10 ml. of anhydrous tetrahydrofuran. After stirring at room temperature for 30 minutes, the reaction mixture was treated with water and worked up by extraction with hexane as in Example 1. The semi-solid residue was treated with hexane and filtered to remove insoluble material. The filtrate was concentrated in vacuo to give 0.72 g. of yellow oil. This material was chromatographed on 30 g. of silica gel. Elution with 9:1 parts by voluem hexane-ether afforded 0.427 g. (62.5%) of an oil. Evaporative distillation yielded rac. benzyl 2,6,10-trimethyl-undeca-4,8-dien-1-yl ether as a colorless liquid, b.p. 110°–115° C. (bath temperature) (0.03 mm Hg.).

EXAMPLE 12 rac. 2,6,10-trimethylundecan-1-ol

A mixture of 0.15 g. (0.5 mmole) of rac. benzyl 2,6,10-trimethylundeca-4,8-dien-1-yl ether, 0.1 g. of 5% by weight palladium on 95% by weight carbon and 10 ml. of ethyl acetate was stirred in an atmosphere of hydrogen for 16 hours at room temperature. The catalyst was filtered and the filtrate was concentrated in vacuo. The oily residue was dissolved in 10 ml. of ethyl acetate and rehydrogenated over 0.1 g. of 5% palladium on carbon, for 5 hours at room temperature. The catalyst was again filtered and the filtrate was concentrated in vacuo. The residue was evaporatively distilled giving 0.092 g. (86%) of rac. 2,6,10-trimethylundecan-1-ol as a colorless oil, b.p. 100°–105° C. (bath temperature) (0.02 mm Hg.).

EXAMPLE 13

S-(+)-tert. Butyl 3-tert.butoxy-2-methylpropionate

A mixture of 40 ml. of liquid isobutylene, 0.91 ml. of 100% phosphoric acid (prepared by dissolving 5 g. of phosphorous pentoxide in 11 ml. of 85% phosphoric acid) and 2 ml. of boron trifluoride etherate was prepared at −70° C. to −75° C. and stirred at this temperature while a solution of 5 g. of a mixture of S-(+)-$\beta$-hydroxyisobutyric acid (~38% by g c analysis) and isobutyric acid (~55% by g c analysis) in 75 ml. of dichloromethane was added over a 5 minute period. The reaction mixture was stirred at −72° C. for 0.5 hour then at 0° C. for 3 hours whereupon it was treated with 95 ml. of water and 5.4 g. of sodium bicarbonate. Work-up with dichloromethane as in Example 1 gave 18 g. of oily product which was chromatographed on 180 g. of silica gel. Elution with 19:1 parts by volume and 9:1 parts by volume hexane-ether yielded 4.7 g. of liquid which was fractionated. There was obtained 2.1 g. (53.3%) of S-(+)-tert.butyl 3-tert. butoxy-2-methylpropionate as a colorless liquid, b.p. 77°–79.5° C. (10 mm Hg.). $[\alpha]^{25} D + 19.74°$ (C 4, $CH_3OH$).

EXAMPLE 14

R-(+)t-tert.Butoxy-2-methyl-1-propanol

To a stirred slurry of 0.352 g. (9.26 mmoles) of lithium aluminum hydride in 13 ml. of anhydrous ether was added a solution of 1 g. (4.63 mmoles) of S-(+)-tert.butyl 3-tert.butoxy-2-methylpropionate in 13 ml. of anhydrous ether, over a 5 min. period, keeping the temperature at 5°–10° C. After stirring at room temperature for 3 hours, the reaction mixture was carefully decomposed by the addition of 0.66 ml. of 10% aqueous sodium hydroxide and 0.73 ml. of water with ice bath cooling. Stirring was continued at room temperature for 15 minutes then the solids were filtered and washed with ether. The filtrate and washes were combined, washed with brine, dried, filtered and concentrated under reduced pressure. The residue (0.663 g.) was chromatographed on 30 g. of silica gel. Elution with 2:1 parts by volume and 1:1 parts by volume hexane-ether yielded a liquid which was evaporatively distlled giving 0.526 g. (77.9%) of R-(+)-tert.butoxy-2-, methyl-1-propanol as a colorless liquid, b.p. 62°–67° C. (bath temperature) (10 mm Hg.); $[\alpha]^{25} D + 0.49°$ (C 4, $CH_3OH$).

EXAMPLE 15

R-(+)-4-tert.Butoxy-3-methylbutyronitrile

A solution of 19.3 g. (0.132 mole) of R-(+)-3-tert.butoxy-2-methyl-1-propanol and 38.6 g. (0.147 mole) of triphenylphosphine in 75 ml. of dichloromethane was stirred with ice bath cooling while 24.9 g. (0.14 mole) of N-bromosuccinimide was added in small portions keeping the temperature below 30° C. The reaction mixture was stirred at room temperature for 1 hour then the dichloromethane was distilled at atmospheric pressure. The bromide was distilled from the residue under reduced pressure giving 23.1 g. of R-(+)-3-tert.-butoxy-2-methyl-1-bromopropane as a colorless liquid, b.p. 62°–65° C. (10 mm Hg.). This material was dissolved in 144 ml. of methanol and 36 ml. of water and treated with 11.07 g. (0.225 mole) of sodium cyanide. The resulting mixture was stirred and heated at reflux for 17 hours, then cooled, diluted with water and worked-up by extraction with dichloromethane and worked up as in Example 1. The crude product (18.9 g.) was chromatographed on 500 g. of silica gel. Elution with 9:1 parts by volume and 4:1 parts by volume hexane-ether gave a liquid which was evaporatively distilled yielding R-(+)-4-tert.butoxy-3-methylbutyronitrile as a colorless liquid, b.p. 88°–90° C. (bath temperature) (11 mm Hg.); $[\alpha]^{25} D + 7.41°$ (C 1.8, $C_6H_6$).

EXAMPLE 16

R-4-tert.Butoxy-3-methylbutanal

R-4-tert.butoxy-3-methylbutanal was prepared starting from R-(+)-4-tert.butoxy-3-methylbutyrontrile using the procedure of Example 6. The crude product was evaporatively distlled giving the R-4-tert.butoxy-3-methylbutanal in 70% yield, as a colorless liquid, b.p. 81°–85° C. (bath temperature) (11 mm Hg.).

EXAMPLE 17

Mixture of (2R,4R)- and (2R,4S)-1-tert.Butoxy-2-methylhept-5-yn-4-ol

The mixture of (2R,4R)-and (2R,4S)-1-tert.butoxy-2-methylhept-5-yn-4-ol was prepared from R-4-tert.butoxy-3-methylbutanal using the procedure of Example 7. The mixture of (2R,4R)-and (2R,4S)-1-tert.butoxy-2-methylhept-5-yn-4-ol was obtained in 83% yield after purification by column chromatography (silica gel; eluted with 2:1 parts by volume and 1:1 parts by volume hexane-ether) and evaporative distillation as a colorless liquid, b.p. 73°–76° C. (bath temperature) (0.1 mm Hg.).

EXAMPLE 18

Mixture of (2R,4R-and (2R,4S)-Z-1-tert.Butoxy-2-methylhept-5-en-4-ol

The mixture of (2R,4R)- and (2R,4S)-1-tert.butoxy-2-methylhept-5-yn-4-ol was hydrogenated using the procedure in Example 8. The crude product was evaporatively distilled giving the mixture of (2R,4R)- and (2R,4S)-Z-1-tert.butoxy-2-methylphept-5-en-4-ol in 90% yield, as a colorless liquid, b.p. 74°–76° C. (bath temperature) (0.1 mm Hg).

EXAMPLE 19

Mixture of (3R,7R)- and (3S,7R)-E-Ethyl 8-tert.butoxy-3,7-dimethyl-4-octenoae

Using the procedure of Example 4, the mixture of (2R,4R)- and (2R,4S)-Z-1-tert.butoxy-2-methylhept-5-en-4-ol was converted into the mixture of (3R,7R)-and (3S,7R)-E-ethyl 8-tert.butoxy-3,7-dimethyl-4-octenoate in 89% yield after purification of the latter by column chromatography (silica gel-eluted with 9:1 parts by volume and 4:1 parts by volume hexane-ether) and evaporative distillation. The mixture of (3R,7R)-and (3S,7R)-E-ethyl-8-tert.butoxy-3,7-dimethyl-4-octenoate was obtained as a colorless oil, b.p. 74°–80° C. (bath temperature) (0.1 mm Hg.); $[\alpha]^{25} D + 5.79°$. (C 2, $C_6H_6$).

EXAMPLE 20

Mixture of (3R,7R)- and (3S,7R)-E-8-tert. Butoxy-3,7-dimethyl-4-octen-1-ol

The mixture of (3R,7R)- and (3S,7R)-E-ethyl 8-tert. butoxy-3,7-dimethyl-4-octenoate was reduced using the procedure described in Example 9. The mixture of (3R,7R)- and (3S,7R)-E-8-tert. butoxy-3,7-dimethyl-4-octen-1-ol was obtained in 85% yield after purification by column chromatography (silica gel - eluted with 2:1 parts by volume and 1:1 parts by volume hexane-ether) and evaporative distillation. The product was a colorless oil, b.p. 74°–77° C. (bath temperature) (0.05 mm Hg.)

EXAMPLE 21

Mixture of (3R,7R)- and (3S,7R)-E-8-tert. Butoxy-3,7-dimethyl-4-octenal

The mixture of (3R,7)- and (3S,7R)-E-8-tert. butoxy-3,7-dimethyl4-octen-1-ol was oxidized using the procedure described in Example 10. The mixture of (3R,7R)- and (3S,7R)-E-8-tert. butoxy-3,7-dimethyl-4-octenal was obtained in 87.3% yield after purification by evaporative distillation, as a colorless oil, b.p. 68°–74° C. (bath temperature) (0.05 mm Hg.).

EXAMPLE 22

Mixture of (2R,6R)- and (2R,6S)-tert.Butyl 2,6,10-trimethylundeca-4,8-dien-1-yl ether The mixture of (2R,6R)- and (2R,6S)-tert. butyl 2,6,10-trimethylundeca-4,8-dien-1-yl ether was prepared starting from the mixture of (3R,7R)- and (3S,7R)-E-8-tert. butoxy-3,7-dimethyl-4-octenal using the procedure described in Example 11. Column chromatography of the crude product (silica gel - eluted with 19:1 parts by volume and 9:1 parts by volume hexane-ether) followed by evaporative distillation gave the mixture of (2R,6R)- and (2R,6S)-tert. butyl 2,6,10-trimethylundeca-4,8-dien-1yl ether in 78% yield, as a colorless oil, b.p. 81°–84° C. (bath temperature) (0.1 mm Hg.); $[\alpha]^{25}D + 6.85°$ (C 1.78, $C_6H_6$).

EXAMPLE 23

Mixture of (2R,6R)- and (2R,6S)- t-Butyl 2,6,10-trimethylundec-1-yl ether

A mixture of 0.459 g. (2.1 mmoles) of a mixture of (2R,6R) - and (2R,6S)-tert. butyl 2,6,10-trimethylundeca-4,8-dien-1-yl ether, 0.2 g. of 5% palladium on carbon and 25 ml. of ethyl acetate was stirred in an atmosphere of hydrogen, at room temperature for 4 hours. The catalyst was filtered and the filtrate was concentrated in vacuo. Evaporative distillation of the residue gave 0.424 g. (91%) of a mixture of (2R,6R)- and (2R,6S)-t-butyl-2,6,10-trimethylundec-1-yl ether as a colorless oil, b.p. 78°–81° C. (bath temperature) (0.06 mm Hg.); $[\alpha]^{25}D + 7.02°$ (C 1.37, $C_6H_6$).

EXAMPLE 24

Mixture of 2R, 6R-2,6,10-Trimethylundecan-1-ol and 2R,6S-2,6,10-Trimethylundecan-1-ol A solution of 0.336 g. (1.24 mmoles) of the mixture of (2R,6R)- and (2R,6S)-t-butyl 2,6,10-trimethylundec-1-yl ether in 7 ml. of trifluoroacetic acid was kept at 0° C. for 6 hours then poured on ice and the resulting mixture was neutralized with 1 N aqueous sodium hydroxide. Extraction with ether and work up as in Example 1 gave 0.366 g. of yellow oil which was dissolved in 10 ml. of 10% methanolic potassium hydroxide. After stirring at room temperature for 1 hour, the solution was neutralized with 1 N aqueous hydrochloric acid and the organic materials were isolated by extraction with ether and worked up as in Example 1. The crude product (0.192 g.) was chromatographed on 10 g. of silica gel. Elution with 9:1 parts by volume, 4:1 parts by volume and 2:1 parts by volume hexane-ether yielded the mixture of 2R,6R-2,6,10-trimethylundecan-1-ol and 2R,6S-2,6,10-trimethylundecan-1-ol which was evaporatively distilled giving 0.159 g. (60%) of this product as a colorless oil, b.p. 74°–78° C. (bath temperature) (0.1 mm Hg.); $[\alpha]^{25}D + 8.42°$ (C 2,hexane).

EXAMPLE 25 rac. 3-Benzyloxy-2-methylpropionitrile

Benzyl alcohol (108 g.; 1 mole) was stirred and treated with 0.3 g. of 50% by weight sodium hydride in a mineral oil dispersion. To the resulting solution was added dropwise 415 ml. (335 g.; 5moles) of methacrylonitrile over a 40 minute period, at room temperature. The reaction mixture was heated at 60°–65° C. for 5 hours then cooled, acidified with 1 N aqueous $H_2SO_4$ and diluted with ether. The ether solution was washed twice with saturated brine then dried, filtered and concentrated in vacuo. Distillation of the residue gave, after removal of low boiling materials, 149.3 g. (85%) of rac. 3-benzyloxy-2-methylpropionitrile as a colorless liquid, b.p. 90°–93° C. (0.02 mm Hg.).

EXAMPLE 26 rac-Methyl 3-benzyloxy-2-methylpropionate

A solution of 50 g. (0.286 mole) of rac. 3-benzyloxy-2-methylpropionitrile in 250 ml. of methanol was cooled in an ice-salt bath and stirred while HCl gas was passed in. After the solution had become saturated with HCl, it was refluxed for 2.25 hours then concentrated under reduced pressure (aspirator). The residue was treated with aqueous $K_2CO_3$ and the resulting alkaline mixture was worked up by ether extraction in the manner of Example 1 giving 52.2 g. of an oil. This material was distilled under reduced pressure yielding rac.-methyl 3-benzyloxy-2-methylpropionate as a colorless liquid, b.p. 88°–90° C. (0.03 mm Hg.).

EXAMPLE 27 rac.-3-benzyloxy-2-methyl-1-propanol

Reduction of the rac.-methyl-3-benzyloxy-2-methylpropionate was carried out with sodium bis(2-methoxyethoxy)-aluminum hydride using the procedure described in Example 9. Distillation of the crude product afforded the rac. 3-benzyloxy-2-methyl-1-propanol in 90.5% yield as a colorless liquid, b.p. 94°–98° C. (0.1 mm Hg.).

EXAMPLE 28 rac.-3-Benzyloxy-2-methylpropionic acid

A solution of 3.2 g. (0.0154 mole) of rac.-methyl-3-benzyloxy-2-methylpropionate in 35 ml. of methanol was stirred at 0° C, while 15.4 ml. of 1 N aqueous NaOH was added dropwise. The reaction mixture was stirred at 0° C. for 1 hour then at room temperature for 2 hours. An additional 1.5 ml. of 1 N aqueous NaOH was then added and stirring was continued for 1.5 hour at room temperature. The resulting solution was diluted with water some NaCl was added and the mixture was extracted with ether. The aqueous solution was acidified with 3 N aqueous HCl and the liberated acid was isolated by ether extraction in the usual manner giving 2.5 g. (84%) of rac.-3-benzyloxy-2-methylpropionic acid as an oil.

EXAMPLE 29 rac.-3-Hydroxy-2-methylpropionic acid

A mixture of 2 g. (0.0103 mole) of rac.-3-benzyloxy-2-methylpropionic acid, 0.5 g. of 5% palladium on carbon and 20 ml. of anhydrous tetrahydrofuran was stirred in atmosphere of hydrogen until 1 mole equivalent of hydrogen was taken up. The catalyst was filtered and washed with $CH_2Cl_2$ then the filtrate and washes were combined and concentrated under reduced pressure. The residue was evaporatively distilled giving 0.88 g. (82%) of rac.-3-hydroxy-2-methylpropionic acid as a viscous, colorless oil, b.p. 105°–110° C. (bath temperature) (0.275 mm Hg.).

EXAMPLE 30 rac. Methyl 3-hydroxy-2-methylpropionate

A solution of 5 g. (0.024 mole) of rac.-methyl 3-benzyloxy-2-methylpropionate in 50 ml. of ethyl acetate was treated with 0.5 g. of 5% by weight palladium on 95% by weight carbon and stirred in an atmosphere of hydrogen. When hydrogen uptake ceased, the catalyst was filtered and washed with ethyl acetate then the filtrate and washes were combined and concentrated under reduced pressure. The residue was evaporatively distilled giving 2.1 g. (74%) of rac. methyl 3-hydroxy-2-methylpropionate as a colorless liquid, b.p. 74°–78° C. (bath temperature) (11 mm Hg.).

EXAMPLE 31 rac.-tert.Butyl 3-tert. butoxy-2-methylpropionate

Treatment of rac.-3-hydroxy-2-methylpropionic acid with isobutylene using the procedure of Example 13 gave the rac.-tert. butyl 3-tert. butoxy-2-methylpropionate in 81.2% yield as a colorless liquid, b.p. 81°–87° C. (bath temperature) (10 mm Hg.)

EXAMPLE 32 rac.-Methyl 3-tert. butoxy-2-methylpropionate

Treatment of hydroxy ester rac. methyl 3-hydroxy-2-methylpropionate with isobutylene using the procedure described in Example 13 gave rac.-methyl 3-tert. butoxy-2-methylpropionate in 43.5% yield as a colorless liquid, b.p. 75°–85° C. (bath temperature) (11 mm Hg.).

EXAMPLE 33 rac.-3-tert. butoxy-2-methyl-1-propanol

Reduction of rac.-tert. butyl 3-tert. butoxy-2-methylpropionate was carried out with lithium aluminum hydride using the procedure described in Example 14. The resulting hydroxy ether, rac.-3-tert. butoxy-2-methyl-1-propanol was obtained in 88% yield as a colorless liquid, b.p. 70°–72° C. (10 mm Hg.).

EXAMPLE 34 rac.-3-tert. Butoxy-2-methyl-1-propanol

Reduction of the ester rac.-methyl 3-tert. butoxy-2-methylpropionate was carried out with lithium aluminum hydride using the procedure described in Example 14. The hydroxy ether, rac-3-tert. butoxy-2-methyl-1-propanol was obtained in 94.2% yield as a colorless liquid, b.p. 70°–80° C. (bath temperature) (10 mm Hg.).

EXAMPLE 35 rac.-3-tert. butoxy-2-methyl-1-bromopropane

Reaction of rac.-3-tert. butoxy-2-methyl-1-propanol with bromine-triphenylphosphine using the procedure of Example 2 gave rac.-3-tert. butoxy-2-methyl-1-bromopropane as a colorless liquid, b.p. 67°–77° C. (bath temperature) (9 mm Hg.).

EXAMPLE 36

Separation of (2R,4R)- and (2R,4S)-1-tert. butoxy-2-methylhept-5-yn-4-ol

A 9.5 g. sample of the Mixture of (2R,4R)- and (2R,4S)-1-tert. butoxy-2-methylhept-5-yn-4-ol prepared as in Example 17 (approximately 1:1) was separated by preparative high pressure liquid chromatography. A 4 ft. × 21 mm. (i.d.) column of silica gel (20-44 μ) was employed with a carrier solvent of 10:1 heptane-ethyl acetate at a flow rate of 40 ml/min and a pressure drop across the column of 800 psi, at room temperature. The sample was injected in 1.5 g. portions. The less polar (4S)-epimer was isolated after one pass (3.55 g.) and was found to be 90% pure (gc). A 0.208 g. sample of this material was further purified by dissolution in ether and stirring at room temperature for 3.5 hour with 10% aqueous silver nitrate solution. The ether solution was separated and processed in the usual manner, then the residue was evaporatively distilled giving pure (2R,4S)-1-tert. butoxy-2-methylhept-5-yn-4-ol (0.189 g.) as a colorless oil, b.p. 88°–94° C. (bath temperature) (0.15 mm Hg.); $[\alpha]^{25}_D$ - 3.10° (c2, $CHCl_3$).

The more polar (4R)-epimer required 3 passes after which there was obtained 2.71 g. Evaporative distillation gave (2R,4R)-1-tert. butoxy-2-methylhept-5-yn-4-ol as a colorless liquid, b.p. 64°–67° C. (bath temperature) (0.02 mm Hg.).

EXAMPLE 37

(2R,4S)-Z-1-tert. Butoxy-2-methylhept-5-en-4-ol

A 1.04 g. (5.26 mmoles) sample of pure (2R,4S)-1-tert. butoxy-2-methylhept-5-yn-4-ol was hydrogenated using the procedure described in Examples 8 and 18. There was obtained (2R,4S)-Z-1-tert. butoxy-2-methylhept-5-en-4-ol as a colorless oil, b.p. 86°–89° C. (bath temperature) (0.15 mm Hg.); $[\alpha]^{25}_D$ - 10.99° (c2, $CHCl_3$).

EXAMPLE 38

(3R,7R)-E-Ethyl 8-tert. butoxy-3,7-dimethyl-4-octenoate

Using the procedure of Examples 4 and 19, (2R,4S)-Z-1-tert. butoxy-2-methylhept-5-en-4-ol was converted into (3R,7R)-E-ethyl 8-tert. butoxy-3,7-dimethyl-4-octenoate which was isolated in 82% yield as a colorless oil, b.p. 74°–78° C. (bath temperature) (0.2 mm Hg.) after evaporative distillation.

EXAMPLE 39

By the procedures of Examples 9, 10, 11, 23 and 24, 3R,7R-E-ethyl 8-tert. butoxy-3,7-dimethyl-4-octenoate is converted to 2R,6R-2,6,10-trimethylundecan-1-ol via the following intermediates:

3R,7R-E-8-tert. butoxy-3,7-dimethyl-4-octen-1-ol;
3R,7R-E-8-tert. butoxy-3,7-dimethyl-4-octenal;
2R,6R-tert. butyl 2,6,10-trimethyl-undeca-4,8-dien-1-yl -ether; and
2R,6R-t-butyl 2,6,10-trimethylundec-1-yl ether.

EXAMPLE 40

(3S,7R)-Ethyl-8-tert. butoxy-3,7-dimethyloctanoate

A mixture of 1.104 g. (4.084 mmoles) of (3R,7R)-Ethyl 8-tert. butoxy-3,7-dimethyl-4-octenoate, a small amount of Raney nickel, and 30 ml. of ethyl acetate was stirred in an atmosphere of hydrogen, at room temperature, for 2 hours during which time approximately one equivalent of hydrogen was taken up. The catalyst was filtered off and washed with ethyl acetate. Concentration of the combined filtrate and washes in vacuo followed by evaporative distillation afforded 1.045 g. (95%) of saturated ester (3S, 7R)-Ethyl 8-tert. butoxy-3,7-dimethyloctanoate as a colorless oil, b.p. 80°–83° C. (bath temperature) (0.15 mm Hg.).

EXAMPLE 41

(3S,7R)-8-tert. Butoxy-3,7-dimethyloctanoic Acid

A solution of 0.108 g. (0.397 mmoles) of (3S,7R)-Ethyl 8-tert. butoxy-3,7-dimethyloctanoate in 2.5 ml. of methanol and 1.5 ml. of 6 N aqueous NaOH was refluxed for 3 hours. The resulting solution was cooled, diluted with water and extracted with diethyl ether. (The ether extract was discarded). The aqueous solution was then acidified with 6 N aqueous HCl and extracted with diethyl ether. The combined ether extracts were washed with water and brine, then dried over anhydrous $MgSO_4$, filtered and concentrated under reduced pressure yielding 0.082 g. of the oily acid (3S,7R)-8-tert. Butoxy-3,7-dimethyloctanoic acid $[\alpha]^{25}D + 4.26°$ (c 2, benzene).

EXAMPLE 42

(3S,7R)-8-tert. Butoxy-3,7-dimethyl-1-octanol

A slurry of 125 mg. (3.28 mmoles) of lithium aluminum hydride in 25 ml. of ether was stirred and cooled in an ice bath while a solution of 893 mg. (3.28 mmoles) of (3S,7R)-Ethyl 8-tert. butoxy-3,7-dimethyloctanoate above, in 25 ml. of ether was added dropwise. After the addition was complete, the reaction mixture was stirred at room temperature for 4 hours then cooled to 0° C. and cautiously decomposed with 0.45 ml. of saturated aqueous sodium sulfate solution. After stirring at room temperature for 19 hours, the mixture was filtered and the filtrate was concentrated under reduced pressure. The crude product (686 mg) was chromatographed on 30 g. of silica gel. Elution with 2:1 and 1:1 parts by volume hexane-ether gave 669 mg. (89%) of (3S,7R)-8-tert. Butoxy-3,7-dimethyl-1-octanol.

EXAMPLE 43

(3S,7R)-8-tert. Butoxy-3,7-dimethyl-1-octanol p-toluenesulfonate

To a stirred solution of 640 mg. (2.78 mmoles) of (3S,7R)-8-tert. Butoxy-3,7-dimethyl-1-octanol in 12 ml. of pyridine at 0° C. was added 1.057 g. (5.56 mmoles) of p-toluenesulfonyl chloride. The resulting mixture was kept at 0° C. for 17 hours, then treated with ice-water and stirred for 30 minutes. The precipiated oil was extracted with diethyl ether and the ether extracts were washed with cold 1 N aqueous HCl, saturated aqueous $NaHCO_3$, water, and saturated brine then dried over anhydrous $MgSO_4$. Filtration and solvent removal in vacuo afforded 1.017 g. (95%) of the (3S,7R)-8-tert. Butoxy-3,7-dimethyl-1-octanol p-toluenesulfonate as a yellow oil.

EXAMPLE 44

(2R,6R)-tert.-Butyl 2,6,10-trimethylundec-1-yl ether

To a stirring and refluxing slurry of 432 mg. (18 mmoles) of magnesium powder in 1 ml. of anhydrous tetrahydrofuran was added a crystal of iodine followed by a few drops of a solution of 2.057 g. (15 mmoles) pf 1-bromo-2-methylpropane in 12 ml. of tetrahydrofuran. After the reaction had begun, the remainder of the bromide solution was added dropwise and when the addition was complete, the mixture was stirred under reflux for 1 hour then cooled to room temperature. A solution of 437 mg. (1.14 mmoles) of (3S,7R)-8-tert. Butoxy-3,7-dimethyl-1-octanol p-toluenesulfonate in 2.5 ml. of tetrahydrofuran was stirred at −78° C. while 1.42 ml. (1.42 mmoles) of the above Grignard solution was added dropwise followed by 0.058 ml. of 0.1 M dilithium tetrachlorocuprate solution in tetrahydrofuran. The resulting mixture was stirred at −78° C. for 10 minutes, then allowed to warm to room temperature over a 2 hour period and stirred for an additional 18 hours. Upon treatment with 1 N aqueous $H_2SO_4$, the organic materials were extracted with ether. The ether extracts were washed with water, saturated aqueous $NaHCO_3$ and saturated brine, combined and dried over anhydrous $MgSO_4$. Filtration and concentration under reduced pressure gave 339 mg. of crude product which was chromatographed on 15 g. of siliva gel. Elution with 19:1 and 9:1 parts by volume hexane/ether afforded 237 mg. of (2R,6R)-tert.-Butyl 2,6,10-trimethylundec-1-yl ether containing about 20% of (3S,7R)-8-tert. butoxy-3,7-dimethyl-1-bromo-octane as an impurity. This material was used for cleavage to the alcohol without further purification.

EXAMPLE 45

(2R,6R)-2,6,10-Trimethylundecan-1-ol

The crude ether (2R,6R)-tert.-Butyl 2,6,10-trimethylundec-1-yl ether (237 mg), at 0° C was stirred and treated with 4 ml. of trifluoroacetic acid. The resulting solution was kept at 0° C. for 17 hours after which time the trifluoroacetic acid was evaporated at reduced pressure. The residue was made alkaline with 20% by weight methanolic KOH then neutralized with 6 N aqueous HCl. The product was isolated by ether extraction in the usual manner giving 181 mg. of silica gel. Elution with 7:3 and 6:4 parts by volume hexane/ether gave 130 mg. (53.3% based on tosylate (3S,7R)-8-tert. Butoxy-3,7-dimethyl-1-octanol p-toluenesulfonate) of pure alcohol (2R,6R)-2,6,10-trimethylundecan-1-ol as a colorless oil; $[\alpha]^{25}D + 8.15°$ (c 2, hexane).

We claim:

1. A process for producing a compound of the formula:

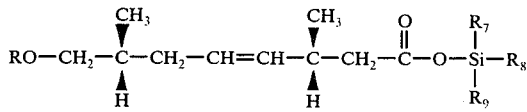

wherein $R_7$, $R_8$ and $R_9$ are lower alkyl, R taken together with the attached oxygen moiety forms an ether protecting group removable by acid catalyzed cleavage or hydrogenolysis;

comprising subjecting an optically active isomer of the formula:

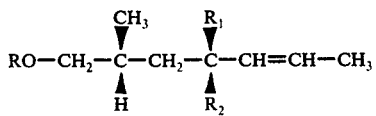
wherein one of $R_1$ and $R_2$ is hydrogen and the other is
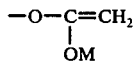
with the proviso that when $R_1$ is hydrogen, the 5-6 double bond has a trans configuration and when $R_2$ is hydrogen, the 5-6 double bond has a cis configuration; and M is an alkali metal;
to Claisen rearrangement by reaction with an agent of the formula:
wherein $R_7$, $R_8$ and $R_9$ are as above; and X is halogen.
* * * * *

UNITED STATES PATENT AND TRADEMARK OFFICE
CERTIFICATE OF CORRECTION

PATENT NO. : 4,107,183
DATED : Aug. 15, 1978
INVENTOR(S) : Noal Cohen and Gabriel Saucy It is certified that error appears in the above-identified patent and that said Letters Patent are hereby corrected as shown below:

Title page under "References Cited",

"Chem. Abstracts Vol. 80, No. 45789j, (1974)"

should be

Chem. Abstracts Vol. 80, No. 45789, (1974)

Signed and Sealed this

Twenty-second Day of January 1980

[SEAL]

Attest:

SIDNEY A. DIAMOND

Attesting Officer     Commissioner of Patents and Trademarks